(12) United States Patent
Gabbay

(10) Patent No.: US 9,439,437 B2
(45) Date of Patent: *Sep. 13, 2016

(54) ANTIMICROBIAL AND ANTIVIRAL POLYMERIC MATERIALS

(75) Inventor: Jeffrey Gabbay, Jerusalem (IL)

(73) Assignee: Cupron Inc., Richmond, VA (US)

( * ) Notice: Subject to any disclaimer, the term of this patent is extended or adjusted under 35 U.S.C. 154(b) by 1032 days.

This patent is subject to a terminal disclaimer.

(21) Appl. No.: 11/648,858

(22) Filed: Dec. 28, 2006

(65) Prior Publication Data

US 2007/0184079 A1    Aug. 9, 2007

Related U.S. Application Data

(63) Continuation of application No. 10/240,993, filed as application No. PCT/IL01/00299 on Apr. 1, 2001, now Pat. No. 7,169,402.

(30) Foreign Application Priority Data

Apr. 5, 2000 (IL) ......................................... 135,487

(51) Int. Cl.
*A01N 57/20* (2006.01)
*A01N 59/20* (2006.01)

(52) U.S. Cl.
CPC ............... *A01N 57/20* (2013.01); *A01N 59/20* (2013.01); *Y10S 2/901* (2013.01); *Y10S 514/841* (2013.01); *Y10S 514/842* (2013.01); *Y10S 514/843* (2013.01)

(58) Field of Classification Search
CPC .............................. A01N 59/20; A01N 25/34
See application file for complete search history.

(56) References Cited

U.S. PATENT DOCUMENTS

| | | | |
|---|---|---|---|
| 252,524 A | 1/1882 | Sagendorf |
| 415,213 A | 11/1889 | Pick |
| 1,210,375 A | 12/1916 | Decker |
| 1,947,451 A | 2/1934 | Barber et al. |
| 2,395,015 A | 2/1946 | Paul et al. |
| 3,014,818 A * | 12/1961 | Wildy ........................... 428/549 |
| 3,300,336 A | 1/1967 | Domenick et al. |
| 3,308,488 A | 3/1967 | Schoonman |
| 3,341,645 A | 9/1967 | Soichiro Horiuchi et al. |
| 3,385,915 A | 5/1968 | Hamling |
| 3,432,589 A | 3/1969 | Drisch |
| 3,494,995 A | 2/1970 | Rainer et al. |
| 3,632,721 A | 1/1972 | Asaeda |
| 3,632,722 A | 1/1972 | Asaeda |
| 3,632,723 A | 1/1972 | Asaeda |
| 3,663,182 A | 5/1972 | Hamling |
| 3,716,615 A | 2/1973 | Bauer et al. |
| 3,720,743 A | 3/1973 | Stevens et al. |
| 3,769,060 A | 10/1973 | Ida et al. |
| 3,821,163 A | 6/1974 | Spivak |
| 3,860,529 A | 1/1975 | Hamling |
| 3,875,141 A | 4/1975 | Drisch |
| 4,072,784 A | 2/1978 | Cirino et al. |
| 4,103,450 A | 8/1978 | Whitcomb |
| 4,115,422 A | 9/1978 | Welch et al. |
| 4,174,418 A | 11/1979 | Welch et al. |
| 4,201,825 A | 5/1980 | Ebneth |
| 4,219,602 A | 8/1980 | Conklin |
| 4,278,435 A | 7/1981 | Ebneth |
| 4,291,086 A | 9/1981 | Auten |
| 4,292,882 A | 10/1981 | Clausen |
| 4,297,117 A | 10/1981 | Holter et al. |
| 4,317,856 A | 3/1982 | Huthelker et al. |
| 4,345,101 A | 8/1982 | Asano et al. |
| 4,361,532 A | 11/1982 | Benai et al. |
| 4,366,202 A | 12/1982 | Borovsky |
| 4,385,632 A | 5/1983 | Odelhog |
| 4,390,585 A | 6/1983 | Holden |
| 4,428,773 A | 1/1984 | Krotz |
| 4,525,410 A | 6/1985 | Hagiwara |
| 4,666,940 A | 5/1987 | Bischoff et al. |
| 4,675,014 A | 6/1987 | Sustmann et al. |
| 4,688,567 A | 8/1987 | Kikuchi et al. |
| 4,710,184 A | 12/1987 | Ehret |
| 4,769,275 A | 9/1988 | Inagaki et al. |
| 4,835,019 A | 5/1989 | White et al. |
| 4,900,618 A | 2/1990 | O'Connor et al. |
| 4,900,765 A | 2/1990 | Murabayashi et al. |
| 4,930,522 A | 6/1990 | Busnel et al. |
| 4,931,078 A | 6/1990 | Yamamoto |
| 4,983,573 A | 1/1991 | Bolt et al. |
| 4,999,240 A | 3/1991 | Brotz |
| 5,009,946 A | 4/1991 | Hatomoto et al. |

(Continued)

FOREIGN PATENT DOCUMENTS

DE    4403016 A1    8/1995
EP    116 865       8/1984

(Continued)

OTHER PUBLICATIONS

*Encyclopedia of Polymer Science and Technology*, John Wiley & Sons, Inc. 8:651-666 and 9:580-598 (1968).

Gabbay et al., "Copper Oxide Impregnated Textiles with Potent Biocidal Activities" Journal of Industrial Textiles, vol. 35, No. 4, 323-35.

*Hands-on Science (H-Sci) Project: Chemical Safety Database*, "Chemical Safety Data: Copper (I) oxide", Comenius—European Cooperation on School Education, downloaded on Jul. 13, 2007 from http://ptcl.chem.ox.ac.uk/-hmclhsci/chemicals/copper_I_oxide.html.

*Hawley's Condensed Chemical Dictionary*, 14th Edition, John Education, downloaded on Wiley & Sons, Inc., Definitions of cuprous oxide and cupric oxide.

"Israeli Breakthriugh Mines Copper to Keep Bacteria Away," ISRAEL21C (revised Feb. 21, 2007) Retrieved Dec. 18, 2008 from URL: http://www.israel21c.org/bin/en.jsp?enScript=PrintVersion.jps&enDispWho=Articles%SE11172.

(Continued)

*Primary Examiner* — Kyle Purdy
(74) *Attorney, Agent, or Firm* — Bernard G. Pike; Pike IP Law, PLLC

(57) ABSTRACT

The invention provides an antimicrobial and antiviral polymeric material, having microscopic particles of ionic copper encapsulated therein and protruding from surfaces thereof.

16 Claims, 2 Drawing Sheets

(56) References Cited

U.S. PATENT DOCUMENTS

Figure 1:
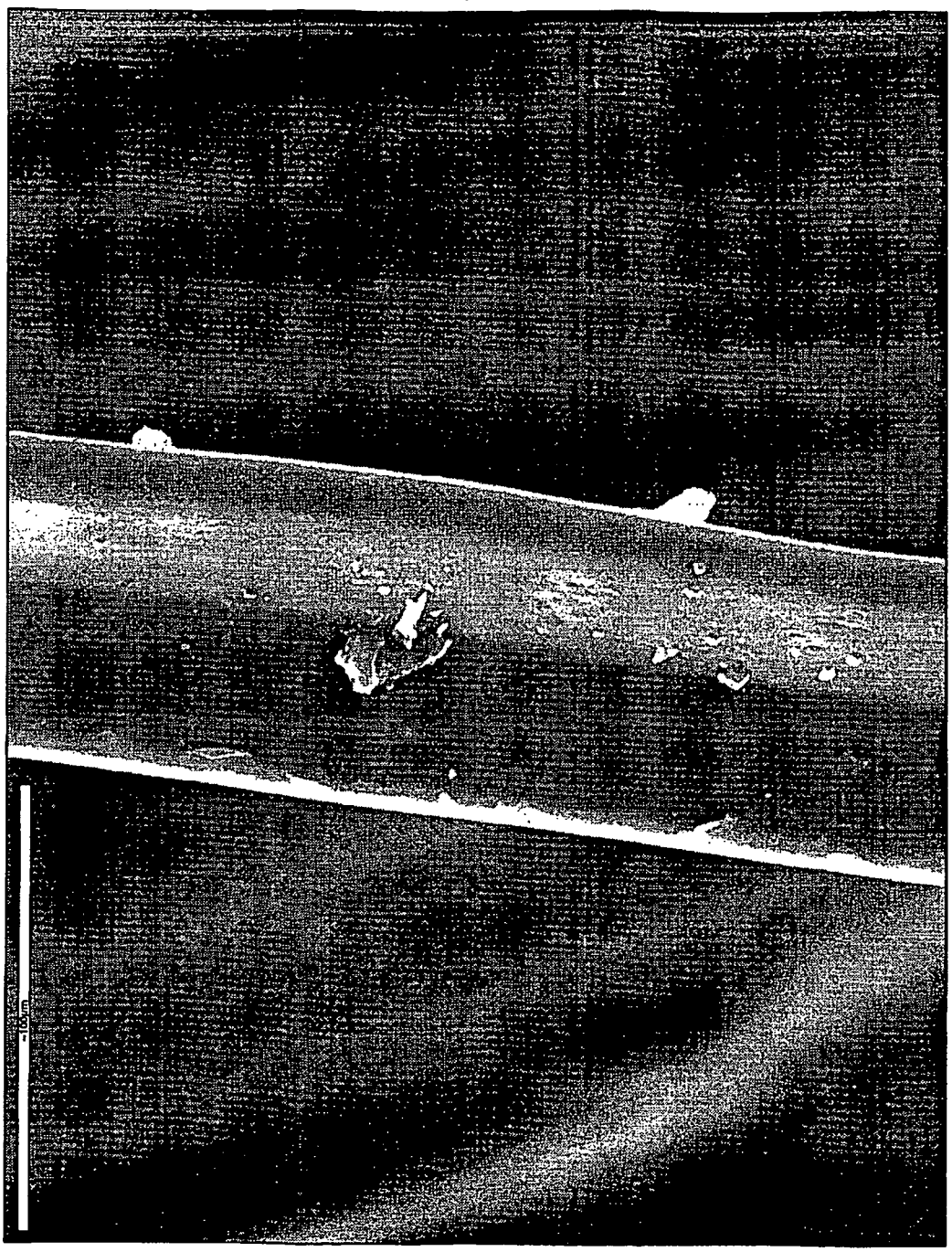

| | | | |
|---|---|---|---|
| 5,017,420 | A | 5/1991 | Marikar et al. |
| 5,024,875 | A | 6/1991 | Hill et al. |
| 5,066,538 | A | 11/1991 | Huykman |
| 5,089,205 | A | 2/1992 | Huang et al. |
| 5,143,769 | A | 9/1992 | Moriya et al. |
| 5,175,040 | A | 12/1992 | Harpell et al. |
| 5,180,402 | A * | 1/1993 | Kubota et al. .................... 8/490 |
| 5,200,256 | A | 4/1993 | Dunbar |
| 5,217,626 | A | 6/1993 | Yahya et al. |
| 5,227,365 | A | 7/1993 | Van Den Sype |
| 5,254,134 | A | 10/1993 | Zhao et al. |
| 5,269,973 | A | 12/1993 | Takahashi et al. |
| 5,280,796 | A | 1/1994 | Rosenberger |
| 5,316,837 | A | 5/1994 | Cohen |
| 5,316,846 | A | 5/1994 | Pinsky et al. |
| 5,370,934 | A | 12/1994 | Burch et al. |
| 5,399,425 | A | 3/1995 | Burch |
| 5,405,644 | A | 4/1995 | Ohsumi et al. |
| 5,407,743 | A | 4/1995 | Clough et al. |
| 5,411,795 | A | 5/1995 | Silverman |
| 5,458,906 | A | 10/1995 | Liang |
| 5,492,882 | A | 2/1996 | Doughty et al. |
| 5,503,917 | A | 4/1996 | Hughes |
| 5,518,812 | A | 5/1996 | Mitchnick et al. |
| 5,547,610 | A | 8/1996 | Mortenson |
| 5,549,972 | A | 8/1996 | Hsu et al. |
| 5,573,021 | A | 11/1996 | Grofcisk et al. |
| 5,690,922 | A | 11/1997 | Mouri et al. |
| 5,744,222 | A | 4/1998 | Sugihara |
| 5,827,524 | A | 10/1998 | Hagiwara et al. |
| 5,848,592 | A | 12/1998 | Sibley |
| 5,849,235 | A | 12/1998 | Sassa et al. |
| 5,856,248 | A | 1/1999 | Weinberg |
| 5,869,412 | A | 2/1999 | Yenni, Jr. et al. |
| 5,871,816 | A | 2/1999 | Tal |
| 5,881,353 | A | 3/1999 | Kamigata et al. |
| 5,904,854 | A | 5/1999 | Shmidt et al. |
| 5,939,340 | A | 8/1999 | Gabbay |
| 5,981,066 | A | 11/1999 | Gabbay |
| 6,013,275 | A | 1/2000 | Konagaya et al. |
| 6,036,839 | A * | 3/2000 | Kohut et al. .................. 205/574 |
| 6,124,221 | A | 9/2000 | Gabbay |
| 6,369,289 | B1 | 4/2002 | Orr |
| 6,383,273 | B1 | 5/2002 | Kepner et al. |
| 6,394,281 | B2 | 5/2002 | Ritland et al. |
| 6,447,677 | B2 | 9/2002 | King |
| 6,479,584 | B1 | 11/2002 | Nakagawa et al. |
| 6,482,424 | B1 | 11/2002 | Gabbay |
| 6,627,676 | B1 | 9/2003 | George et al. |
| 6,681,765 | B2 | 1/2004 | Wen |
| 6,733,556 | B1 | 5/2004 | Luigi |
| 6,770,331 | B1 | 8/2004 | Mielke et al. |
| 6,861,002 | B2 | 3/2005 | Hughes |
| 6,989,342 | B2 | 1/2006 | Yang |
| 7,067,444 | B2 | 6/2006 | Luo et al. |
| 7,169,402 | B2 * | 1/2007 | Gabbay .................. A01N 57/20 |
| | | | 128/844 |
| 7,192,602 | B2 | 3/2007 | Fechner et al. |
| 7,296,690 | B2 | 11/2007 | Gabbay |
| 7,364,756 | B2 | 4/2008 | Gabbay |
| 7,626,072 | B2 | 12/2009 | Mocadlo |
| 2003/0152610 | A1 | 8/2003 | Rolf |
| 2003/0199018 | A1 | 10/2003 | Gabbay |
| 2004/0105894 | A1 | 6/2004 | Gupta |
| 2004/0167483 | A1 | 8/2004 | Gabbay |
| 2004/0167484 | A1 | 8/2004 | Gabbay |
| 2004/0167485 | A1 | 8/2004 | Gabbay |
| 2004/0180093 | A1 | 9/2004 | Burton et al. |
| 2004/0197386 | A1 | 10/2004 | Gabbay |
| 2004/0208902 | A1 | 10/2004 | Gupta |
| 2004/0247653 | A1 | 12/2004 | Gabbay |
| 2005/0049370 | A1 | 3/2005 | Gabbay |
| 2005/0150514 | A1 | 7/2005 | Gabbay |
| 2008/0193496 | A1 | 8/2008 | Gabbay |
| 2008/0241530 | A1 | 10/2008 | Gabbay |
| 2008/0255285 | A1 | 10/2008 | Gabbay |
| 2008/0311165 | A1 | 12/2008 | Gabbay |
| 2009/0010969 | A1 | 1/2009 | Gabbay |

FOREIGN PATENT DOCUMENTS

| | | | |
|---|---|---|---|
| EP | 116825 A1 | 8/1984 | |
| EP | 0 253 663 A | 1/1988 | |
| EP | 253653 | 1/1989 | |
| EP | 0 427 858 A | 5/1991 | |
| EP | 1 272 037 B1 | 3/2004 | |
| EP | 1978138 A2 | 10/2008 | |
| EP | 1657980 B1 | 5/2009 | |
| FR | 1499358 A | 9/1996 | |
| FR | 2764518 | 6/1997 | |
| GB | 415213 | 8/1934 | |
| GB | 1382820 | 12/1971 | |
| JP | 63-088007 | 4/1988 | |
| JP | 01-046465 | 2/1989 | |
| JP | 01-246204 | 10/1989 | |
| JP | 02-161954 | 6/1990 | |
| JP | 03-113011 | 5/1991 | |
| JP | 4011017 A | 1/1992 | |
| JP | 4058876 A | 2/1992 | |
| JP | 3097909 A | 4/1992 | |
| JP | 05-005108 | 1/1993 | |
| JP | 8-113874 A | 5/1996 | |
| JP | 08268823 A * | 10/1996 | ............. A01N 59/16 |
| WO | WO94/15463 A1 | 7/1994 | |
| WO | WO98/06508 A1 | 2/1998 | |
| WO | WO98/06509 A1 | 2/1998 | |
| WO | WO00/75415 A1 | 12/2000 | |
| WO | WO01/28337 A2 | 4/2001 | |
| WO | WO01/74166 | 10/2001 | |
| WO | WO01/81671 | 11/2001 | |
| WO | WO03/035973 A1 | 5/2003 | |
| WO | WO 03/055941 A1 | 7/2003 | |
| WO | WO 03/086478 A1 | 10/2003 | |
| WO | WO/2005-020689 A1 | 3/2005 | |
| WO | WO2006/048879 A1 | 5/2006 | |
| WO | WO2008/117277 A2 | 10/2008 | |

OTHER PUBLICATIONS

Lucata Building Materials, downloaded Jul. 13, 2007 from http://www.luvata.com/Products-and-Services/Markets-We-Serve/Architecture-and-Building/Building-Materials/.

Marino et al., "Electronichemical Properties of Silver-Nylon Fabrics," *J. Electrochem. Soc.*, 132(1):68-72 (1985).

Material Saftey Data Sheet # C5971: Cuprous Oxide Number, Effective Date: Feb. 26, 2007, downloaded from http://www.jtbaker.com/msds/englishhtmllc5971.htm.

Application No. PCT/IL01/00299, Inernational Search Report mailed Sep. 19, 2001.

Gugumus F., "Aspects of the stabilization mechanisms of phenolic antioxidants in polyolefins", Macromolecular Materials and Engineering, vol. 137 Issue 1, pp. 189-225 Published Online: Mar. 12, 2003.

Lower S. E., "Calcium stearate in resins and resinous polymers: part 2", Pigment & Resin Technology, vol. 25 Iss: 2, Abstract only, 1993.

Webster Online Dictionary http://www.websters-onlinedictionary.org/definitions/petrolatum?cx=partner-pub-0939450753529744%3AvOqd01-tdlq&cof=FORID%3A9&ie=UTF-8&q=petrolatum&sa=Search#906.

US 7,284,669, 10/2007, Gabbay (withdrawn)

* cited by examiner

ANTIMICROBIAL AND ANTIVIRAL POLYMERIC MATERIALS

The present invention relates to an antimicrobial and antiviral polymeric material and to a process for preparing the same. More particularly, the present invention relates to an antimicrobial polymeric material useful as a wrapping material for agricultural produce, as well as to an antiviral polymeric material useful for the formation of a condom sheath, surgical tubing and surgical gloves.

A problem faced by all food exporters is the attack on the agricultural produce after it has been harvested by microorganisms while in transport. This is especially true when the transportation is measured in days, weeks, or months, rather than hours. Microorganisms are known to cause severe damage to the produce, resulting in added costs which are passed on to the consumer. An example of this is the strawberry harvest in Israel. Every year about 50% of the harvest is lost while in transportation due to the attack of microorganisms. To date, there has been no effective system developed that can effectively reduce the waste rate.

There are many wrapping materials used in food transport from burlap bags to sophisticated polymer wrappings that demonstrate qualities such as strength, flexibility, breathability and are inexpensive. However, none to date are able to control the growth of microorganisms that flourish in packaged, agricultural produce.

According to the present invention it has now been discovered that by adding a small percentage of $Cu^{++}$ in powder form to the slurry of a polymer to be formed into a wrapping material, the package is rendered antimicrobial.

It has also been surprisingly discovered that by adding $Cu^{++}$ in powder form to the slurry of a polymer to be formed into a condom there is produced a condom which inhibits and reduces active HIV-1 in body fluids.

Similarly, surgical gloves and surgical tubing having antimicrobial and antiviral properties can be prepared according to the present invention.

In both WO 98/06508 and WO 98/06509 there are taught various aspects of a textile with a full or partial metal or metal oxide plating directly and securely bonded to the fibers thereof, wherein metal and metal oxides, including copper, are bonded to said fibers.

More specifically, in WO 98/06509 there is provided a process comprising the steps of: (a) providing a metallized textile, the metallized textile comprising: (i) a textile including fibers selected from the group consisting of natural fibers, synthetic cellulosic fibers, regenerated fibers, acrylic fibers, polyolefin fibers, polyurethane fibers, vinyl fibers, and blends thereof, and (ii) a plating including materials selected from the group consisting of metals and metal oxides, the metallized textile characterized in that the plating is bonded directly to the fibers; and (b) incorporating the metallized textile in an article of manufacture.

In the context of said invention the term "textile" includes fibers, whether natural (for example, cotton, silk, wool, and linen) or synthetic yarns spun from those fibers, and woven, knit, and non-woven fabrics made of those yarns. The scope of said invention includes all natural fibers; and all synthetic fibers used in textile applications, including but not limited to synthetic cellulosic fibers (i.e., regenerated cellulose fibers such as rayon, and cellulose derivative fibers such as acetate fibers), regenerated protein fibers, acrylic fibers, polyolefin fibers, polyurethane fibers, and vinyl fibers, but excluding nylon and polyester fibers, and blends thereof.

Said invention comprised application to the products of an adaptation of technology used in the electrolyses plating of plastics, particularly printed circuit boards made of plastic, with metals. See, for example, Encyclopedia of Polymer Science and Engineering (Jacqueline I. Kroschwitz, editor), Wiley and Sons, 1987, vol. IX, pp 580-598. As applied to textiles, this process included two steps. The first step was the activation of the textile by precipitating catalytic noble metal nucleation sites on the textile. This was done by first soaking the textile in a solution of a low-oxidation-state reductant cation, and then soaking the textile in a solution of noble metal cations, preferably a solution of $Pd^{++}$ cations, most preferably an acidic $PdCl_2$ solution. The low-oxidation-state cation reduces the noble metal cations to the noble metals themselves, while being oxidized to a higher oxidation state. Preferably, the reductant cation is one that is soluble in both the initial low oxidation state and the final high oxidation state, for example $Sn^{++}$, which is oxidized to $Sn^{++++}$, or $Ti^{+++}$, which is oxidized to $Ti^{++++}$.

The second step was the reduction, in close proximity to the activated textile, of a metal cation whose reduction was catalyzed by a noble metal. The reducing agents used to reduce the cations typically were molecular species, for example, formaldehyde in the case of $Cu^{++}$. Because the reducing agents were oxidized, the metal cations are termed "oxidant cations" herein. The metallized textiles thus produced were characterized in that their metal plating was bonded directly to the textile fibers.

In WO 98/06508 there is described and claimed a composition of matter comprising:

(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and (b) a plating including materials selected from the group consisting of metals and metal oxides;

the composition of matter characterized in that said plating is bonded directly to said fibers.

Said publication also claims a composition of matter comprising:

(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and.

(b) a plurality of nucleation sites, each of said nucleation sites including at least one noble metal;

the composition of matter characterized by catalyzing the reduction of at least one metallic cationic species to a reduced metal, thereby plating said fibers with said reduced metal.

In addition, said publication teaches and claims processes for producing said products.

A preferred process for preparing a metallized textile according to said publication comprises the steps of:

a) selecting a textile, in a form selected from the group consisting of yarn and fabric, said textile including fibers selected from the group consisting of natural fibers, synthetic cellulosic fibers, regenerated protein fibers, acrylic fibers, polyolefin fibers, polyurethane fibers, vinyl fibers, and blends thereof;

b) soaking said textile in a solution containing at least one reductant cationic species having at least two positive oxidation states, said at least one cationic species being in a lower of said at least two positive oxidation states;

c) soaking said textile in a solution containing at least one noble metal cationic species, thereby producing an activated textile; and d) reducing at least one oxidant cationic species in a medium in contact with said activated textile, thereby producing a metallized textile.

Said publications, however, are limited to coated fibers and textiles prepared according to said processes and do not teach or suggest the possibility of incorporating ionic copper into a polymeric slurry whereby there are produced films and fibers having microscopic particles of ionic copper encapsulated therein and protruding therefrom and having antimicrobial and antiviral polymeric properties, as described and exemplified herein.

With this state of the art in mind there is now provided according to the present invention an antimicrobial and antiviral polymeric material, having microscopic particles of ionic copper encapsulated therein and protruding from surfaces thereof.

In another aspect of the present invention there is provided a process for preparing an antimicrobial and antiviral polymeric material, comprising preparing a polymeric slurry, introducing an ionic copper powder and dispersing the same in said slurry and then extruding said slurry to form a polymeric material wherein particles of said ionic copper are encapsulated therein and protrude from surfaces thereof.

The polymeric material of the present invention can be in the form of a film, a fiber, or a yarn, wherein said films are used per se and said fibers and yarns can be formed into a packaging material for agricultural products.

Said material can be made from almost any synthetic polymer, which will allow the introduction of an anionic, copper dust into its liquid slurry state. Examples of some materials are polyamides (nylon), polyester, acrylic, polypropylene, silastic rubber and latex. When the copper dust is ground down to fine powder, e.g., a size of between 1 and 10 microns and introduced into the slurry in small quantities, e. g., in an amount of between 0.25 and 10% of the polymer weight, it was found that the subsequent product produced from this slurry exhibited both antimicrobial and antiviral properties.

Unlike the fibers described, e. g. in WO 98106508 and WO 98/06509, in which the fibers are coated on the outside, in the present product the polymer has microscopic particles of ionic copper encapsulated therein and protruding from surfaces thereof. These particles which protrude from the surface of the polymeric material have been shown to be active, as demonstrated by the tests set forth hereinafter.

In general, the products of the present invention are produced as follows:
1. A slurry is prepared from any polymer, the chief raw material preferably being selected from a polyamide, a polyethylene, a polyurethane and a polyester. Combinations of more than one of said materials can also be used provided they are compatible or adjusted for compatibility. The polymeric raw materials are usually in bead form and can be mono-component, bi-component or multi-component in nature. The beads are heated to melting at a temperature which preferably will range from about 120 to 180° C.
2. At the hot mixing stage, before extrusion, a powder of ionic copper is added to the slurry and allowed to spread through the heated slurry. The particulate size will be preferably between 1 and 10 microns, however can be larger when the film or fiber thickness can accommodate larger particles.
3. The liquid slurry is then pushed with pressure through holes in a series of metal plates formed into a circle called a spinneret. As the slurry is pushed through the fine holes which are close together, they form single fibers or if allowed to contact one another, they form a film or sheath. The hot liquid fiber or film is pushed upward with cold air forming a continuous series of fibers or a circular sheet. The thickness of the fibers or sheet is controlled by the size of the holes and speed at which the slurry is pushed through the holes and upward by the cooling air flow.
4. In percentage mixtures of up to 10% by weight of ionic copper dust demonstrated, no degradation of physical properties in a polyamide slurry of the finished product. When tested, mixtures as low as 1% still showed antimicrobial properties, as well as surprisingly showing inhibition of HIV-1 activity.

Referring to the use of the material as a post harvest packaging system, it was found that microbes outside the package will not be able to enter the enclosed area and that microbes inside the packet will have difficulty in growing along the inside of the packaging material which is usually where they incubate due to condensation within the encapsulated area.

As indicated hereinabove, the polymeric material of the present invention, having microscopic particles of ironic copper encapsulated therein, can also be utilized to manufacture disposable gloves and condoms using a mold/form configuration.

In general, the chief raw material is concentrated and preserved natural rubber latex. In addition such chemicals as acid, chlorine gases, alkalis, and corn/maize starch can be added, as is known in the art, however according to the present invention there is also added CU++ in powder form.

Formers (or positive molds) are prepared through preparations that will keep the liquid latex from sticking thereto. This is done through a series of dips and treatments to the molds, as known per se in the art. The formers are then cleaned and dried and are dipped into a solution of coagulant chemicals. The coagulant forms a layer on the formers which helps to solidify latex when the formers are dipped into the latex tank.

The formers are dipped into the latex mixture, withdrawn therefrom and passed through a curing oven. The gloves and/or condoms will be vulcanized as they pass through the different areas of the oven which expose the same to temperatures ranging from about 120 to 140° C. This process cross-links the latex rubber to impart the physical qualities required.

The difference between the normal process of manufacturing a disposable glove/condom and the process of the present invention is the addition of the Cu++ powder in the raw materials.

While the invention will now be described in connection with certain preferred embodiments in the following examples and with reference to the attached figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Figure 2:
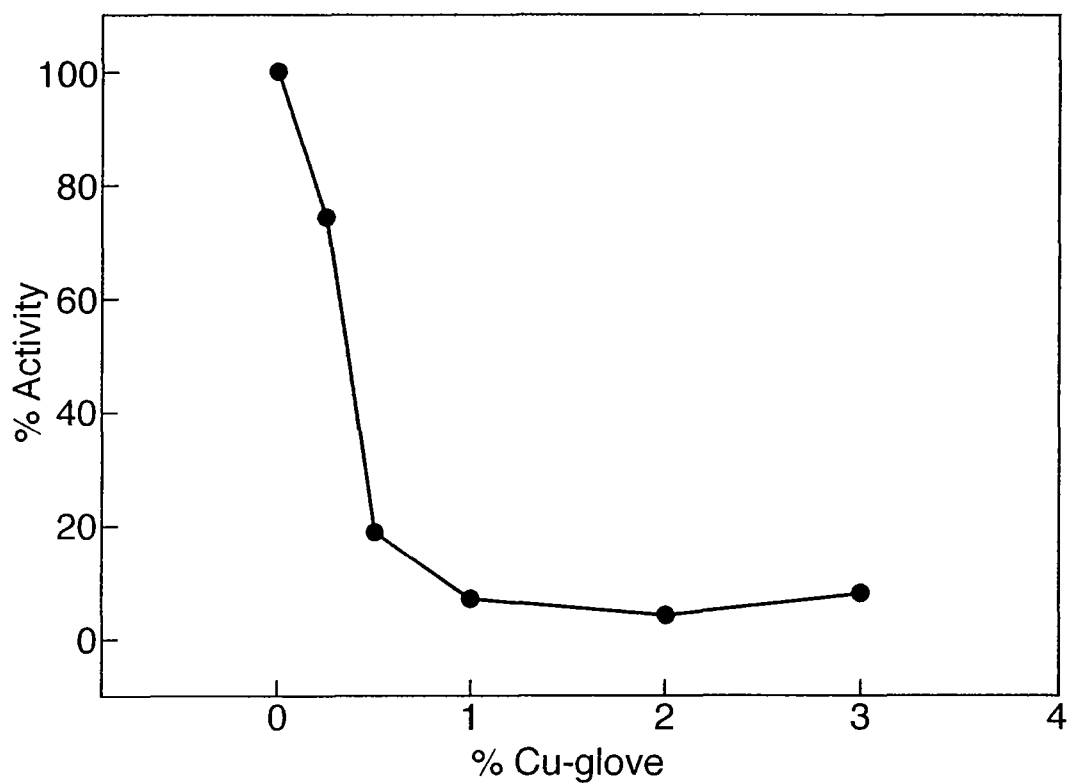

In the drawings:

FIG. 1 is an electron microscope photograph of a nylon fiber with copper particles embedded therein and protruding therefrom after having been added to a polymeric slurry; and FIG. 2 is a graphical representation of the inhibition of HIV-1 on sterilized pieces of latex gloves impregnated with varying amounts of ionic copper according to the present invention.

EXAMPLE 1

Preparation of Fibers

A total of 500 grams of a polyamide bi-component compound were prepared by heating the two beaded chemicals in separate baths each at 160° C.

The two separate components were then mixed together and allowed to stir for 15 minutes until the mixture appeared to be homogenous in color.

The mixed chemistry was again divided into two separate pots. In one pot, 25 grams of a mixture of CuO and $Cu_2O$ powder was added yielding a 1% mixture. In the second pot 6.25 grams of a mixture of CuO and $Cu_2O$ were added yielding a 0.25% mixture. In both cases, the temperature of 160° C. was maintained. The compounds were stirred until they appeared homogenous in color.

The two mixtures were run through a spinneret with holes that yielded fibers of between 50 and 70 microns in diameter. Since the Cu++ releasing powder was ground to particles of less than 20 microns no obstructions in the spinneret holes were observed. The extruded fibers were air-cooled and spun on to cones.

The fibers were tested for biological activity.

The difference between the normal process of manufacturing any synthetic fiber and this process is the addition of the Cu++ releasing powder in the raw materials.

EXAMPLE 2

100 μl aliquots of highly concentrated HIV-1 virus were incubated on top of the fibers for 30 minutes at 37° C. Then 10 μl of each pretreated virus were added to MT-2 cells (Lymphocyte Human Cell Line) cultured in 1 ml media. The cells were then incubated for 5 days in a moist incubator at 37° C. and the virus infectivity and proliferation was determined by measuring the amount of p24 (a specific HIV-1 protein) in the supernatant with a commercial ELISA (Enzyme Based Immuno-absorption Assay) kit. The results are the average of duplicate experiments. As control for possible cytotoxicity of the CuO or $Cu_2O$ to the cells, similar experiments were carried out as above, but the fibers were incubated with 100 μl of natural medium that did not contain HIV-1. No cytotoxicity was observed, i.e., none of the host cells were observed to be killed, under the experimental conditions described above.

The following summarizes the evaluation of the capacity of the several fibers impregnated with CuO and $Cu_2O$ to inhibit HIV-1 proliferation in tissue culture:

| | |
|---|---|
| Negative control (Polymeric Fiber without CuO and $Cu_2O$): | no inhibition |
| Positive control (CuO and $Cu_2O$ powder): | 70% inhibition |
| 1% CuO and $Cu_2O$ Fiber: | 26% inhibition. |

EXAMPLE 3

Antifungal Susceptibility Testing

Susceptibility testing was performed as follows:

Agar formulation used for this test was chosen in accordance with NCCLS document M27-A: RPMI (RPG) and a buffered to pH 7.0 with 0.165 M morpholinepropanesulfonic acid buffer (MOPS).

For the test, 90-mm-diameter plates containing agar at a depth of 4.0 mm were used. For *Candida albicans, Cryptococcus neoformans, micrococcus, Tinea pedis,* and *Tinea curpus,* the inoculum was prepared from a 24 hour culture and a 48 hour culture respectively; whereas for *Aspergillus fumigatus* and *Trichophyton mentagrophytes* a five-day old culture was used. Cell suspension was prepared in sterile 0.85% NaCl adjusted to a turbidity of a 0.5 McFarland standard. The agar surface was inoculated by streaking a nontoxic swab dipped in a cell suspension across the entire surface of the agar in three directions.

After excess moisture was absorbed into the agar and the surface was completely dry, Chemtex/MTC treated fibers in a concentration range from 3%-10% were applied to each plated. The plates were incubated at 35° C. and read after 24 hours, 48 hours, and 7 days. Antifungal activity of the treated fibers was considered positive if a zone of inhibition was visible underneath and surrounding the fibers.

Antibacterial Susceptibility Testing

Susceptibility testing was performed as described above for the antifungal activity with the following modifications: Mueller-Hinton agar (Difco, Detroit, Mich.) was the medium used. The pH was adjusted to 7.2-7.4. The bacteria used for this study were *Escherichia coli, Staphylococcus aureus, brevubacterium, acinetobacter* and *micrococcus.*

Results

The treated fibers in a concentration range of 3-10% exhibited characteristic inhibitory zone underneath and surrounding the fibers, indicating correct antifungal and antibacterial activity. The controls (untreated fibers) indicated no antifungal or antibacterial activity.

EXAMPLE 4

Fifty μl of RPMI 1640 medium, containing HIV-I IIIB (laboratory T-tropic strain, 0.36 pg p24 [amount of virus]), were placed on top of UV sterilized pieces of gloves. As negative control for viral activity, 50 μl of medium was placed on the gloves, and as positive control, virus was placed on a regular glove (i.e. no Cu++). The experiment was done in duplicates, i.e., in each glove (different concentrations of Cu++) two separate drops with or without virus were placed.

After 20 minutes of incubation at room temperature, the 50 μl of drops containing the virus were mixed with 450 μl fresh medium (containing 10% fetal calf serum), and the mixture was added to $2 \times 10^5$ MT-2 cells (a lymphocyte cell line) in 1 ml medium (containing 10% fetal calf serum).

The virus-cell mixtures were then incubated in 24 well plates in a $CO_2$ humidified incubator at 37° C. After 4 days of incubation the amount of virus present per well was quantified by a Reverse Transcriptase (RT) Assay.

RT is a key enzyme of the HIV-I, which can polymerize a DNA strand from an RNA strand. By adding radio-labeled deoxynucleotides, the amount of newly synthesized DNA can be quantified. The percentage of inhibition as shown in FIG. 2 was calculated by dividing the average counts per minute (CPM) obtained in each glove concentration by that obtained in the regular control glove. As will be noted from said graph, twenty minutes of exposure of concentrated HIV-1 virus to the surface of a latex glove impregnated with 1% or more of a copper ion yielding compound at room temperature resulted in a more than a 95% neutralization of subsequent virus infectivity of lymphocytes (the main target of HIV-1). This result points out the potential of an approach of impregnating copper into a slurry to form a glove or other item, such as a condom, to neutralize infectious viruses which may be found in human contaminated fluids such as blood or sperm.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for preparing an antimicrobial and antiviral polymeric material containing cupric oxide and cuprous oxide as an anti-microbial and anti-viral agent responsible for the antimicrobial and antiviral activity of the polymeric material, comprising preparing a polymeric slurry, introducing a plurality of microscopic antimicrobial and antiviral particles to the polymeric slurry, wherein the particles comprise an antimicrobial and antiviral agent consisting of cupric oxide and cuprous oxide, wherein said particles are of a size of between 1 and 10 microns, dispersing the particles in said slurry and then extruding said slurry to form a polymeric material wherein said particles are incorporated in the polymer, wherein a portion of said particles in said polymer are exposed and protruding from the surface of the material and release $Cu^{++}$ ions when exposed to water or water vapor to provide the antimicrobial and antiviral activity of the polymeric material.

2. The process of claim 1 wherein the particles are introduced into the slurry in an amount of between 0.25 and 10% of the polymer weight.

3. The process of claim 1 wherein the polymeric material is a fiber.

4. The process of claim 1 wherein the polymeric material is a film.

5. A process for preparing an antimicrobial and antiviral polymeric material containing cupric oxide and cuprous oxide as an anti-microbial and anti-viral agent responsible for the antimicrobial and antiviral activity of the polymeric material, comprising:
preparing a polymeric slurry,
introducing a plurality of microscopic water insoluble particles into the polymeric slurry, wherein said particles comprise an antimicrobial and antiviral agent consisting of a mixture of cupric oxide and cuprous oxide, and
wherein said particles have a size in the range of between 1 and 10 microns and are introduced in an amount that is between 0.25 and 10% of the polymer weight,
dispersing the particles in said slurry, and then
extruding said slurry to form a polymeric material wherein said particles are incorporated in the polymer, and wherein a portion of said particles in said polymer are exposed and protruding from the surface of the material and release $Cu^{++}$ ions when exposed to water or water vapor.

6. The process of claim 1 wherein the polymer comprises polyamide, polyester, or polypropylene.

7. The process of claim 2 wherein the polymer comprises polyamide, polyester, or polypropylene.

8. The process of claim 3 wherein the polymer comprises polyamide, polyester, or polypropylene.

9. The process of claim 4 wherein the polymer comprises polyamide, polyester, or polypropylene.

10. The process of claim 5 wherein the polymer comprises polyamide, polyester, or polypropylene.

11. A process for preparing an antimicrobial and antiviral polymeric material, comprising:
preparing a polymeric slurry,
introducing a $Cu^{++}$ releasing antibacterial agent, wherein said agent consists of cupric oxide and cuprous oxide particles, and wherein said particles have a size in the range of between 1 and 10 microns and are introduced in an amount that is between 0.25 and 10% of the polymer weight,
dispersing the particles in said polymeric slurry, and then
extruding said slurry to form a polymeric material
wherein said particles are incorporated in the polymer, and wherein a portion of said particles in said polymer are exposed and protruding from the surface of the material and release $Cu^{++}$ ions when exposed to water or water vapor.

12. A process for preparing an antimicrobial polymeric material, comprising preparing a polymeric slurry, adding $Cu^{++}$-releasing copper oxide particles as an antimicrobial component, wherein the particles comprise an antimicrobial agent and the antimicrobial agent consists of cupric oxide and cuprous oxide, wherein said particles are of a size of between 1 and 10 microns and are added in an amount that is between 0.25 and 10% of the polymer weight, dispersing the particles in said slurry and then extruding said slurry to form a polymeric material wherein said particles are incorporated in the polymer, wherein a portion of said particles in said polymer are exposed and protruding from the surface of the material and release $Cu^{++}$ ions when exposed to water or water vapor.

13. The process of claim 12 wherein the polymer comprises polyamide, polyester, or polypropylene.

14. The process of claim 13 wherein the polymeric material is a fiber.

15. The process of claim 12 wherein the antibacterial agent consisting of cupric oxide and cuprous oxide is the source of antimicrobial activity of the polymeric material.

16. A process for preparing an antimicrobial polymeric fibers, comprising
a) preparing a polymeric slurry,
b) adding an antimicrobial agent consisting of $Cu^{++}$ releasing copper oxide particles, wherein said particles are of a size of between 1 and 10 microns and are added in an amount that is between 0.25 and 10% of the polymer weight,
c) dispersing the particles in said slurry and then
d) extruding said slurry to form polymeric fibers wherein said particles are incorporated in the polymer, wherein a portion of said particles in said polymer are exposed and protruding from the surface of the material and release $Cu^{++}$ ions when exposed to water or water vapor wherein the polymeric fibers when extruded have greater antimicrobial activity than polymeric fibers prepared the same way except without addition of $Cu^{++}$-releasing copper oxide particles.

* * * * *